United States Patent [19]

Spinello

[11] Patent Number: 5,078,924
[45] Date of Patent: Jan. 7, 1992

[54] APPARATUS AND METHOD FOR VERIFIABLY STERILIZING, DESTROYING AND ENCAPSULATING REGULATED MEDICAL WASTES

[76] Inventor: Ronald P. Spinello, 523 Post Ave., Westbury, N.Y. 11590

[21] Appl. No.: 531,943

[22] Filed: Jun. 1, 1990

Related U.S. Application Data

[63] Continuation-in-part of Ser. No. 364,978, Jun. 9, 1989, Pat. No. 4,992,217.

[51] Int. Cl.⁵ .............................................. A61L 11/00
[52] U.S. Cl. ...................... 264/0.5; 252/628; 422/294; 422/307
[58] Field of Search .......... 209/930; 252/628; 264/0.5; 422/22, 294, 307; 424/1.1; 427/4, 331; 523/129; 524/1

[56] References Cited

U.S. PATENT DOCUMENTS

| | | | |
|---|---|---|---|
| 3,476,506 | 11/1969 | Andersen et al. | 422/294 |
| 3,892,706 | 7/1975 | Jetzer | 523/129 |
| 4,409,029 | 10/1983 | Larker et al. | 264/0.5 |
| 4,434,074 | 2/1984 | Fox et al. | 252/628 |
| 4,662,516 | 5/1987 | Baker, Sr. et al. | 206/363 |
| 4,756,681 | 7/1988 | Unger et al. | 264/0.5 |
| 4,834,917 | 5/1989 | Ramm et al. | 252/628 |
| 4,992,217 | 2/1991 | Spinello | 252/628 |

Primary Examiner—Richard W. Wendtland
Attorney, Agent, or Firm—Hoffmann & Baron

[57] ABSTRACT

Apparatus and method for sterilizing and encapsulating contaminated waste particularly medical implement waste in which a volume of thermoplastic compound having a melting point temperature-calibrated at a value which corresponds substantially to the temperature at which all biological contamination is rendered sterile substantially on contact, and impregnating a space containing contaminated waste items with the liquid compound and thereafter cooling the mass to its solidified phase while containing it against protrusion of any waste item. Two stage treatment of the waste is effected by utilizing a second calibrated thermoplastic having a lower melting temperature in a common deformable waste container with the first thermoplastic. The container is locked in a first geometry by means of the first thermoplastic so that preliminary heating liquefies the second thermoplastic to at least partially encapsulate and sterilize successive charges of waste, while simultaneously creating additional space in the container to receive the subsequent charges of waste. When the container is heated to a final elevated temperature it is released from its initial geometry by the liquefaction of the first thermoplastic to complete the final encapsulation and sterilization process.

30 Claims, 8 Drawing Sheets

APPARATUS AND METHOD FOR VERIFIABLY STERILIZING, DESTROYING AND ENCAPSULATING REGULATED MEDICAL WASTES

RELATED APPLICATIONS

This is a continuation in part of the Applicant's pending application Ser. No. 07/364,978 filed June 9, 1989, now U.S. Pat. No. 4,992,217.

The invention is directed to safe handling and disposal of regulated medical waste such as medical implement waste from hospitals, health care facilities and dental and medical offices. It is particularly concerned with safely processing contaminated needles, scalpels, glass vials and like sharp metal or glass objects which have invaded the human body or received body fluids, as well as used thermoplastic hypodermic syringe barrels, all of which are difficult and dangerous to handle, destroy or eventually store.

BACKGROUND OF THE INVENTION

Environmental protection laws at all levels of government are concerned with contaminated medical wastes also now known as regulated medical wastes. In most jurisdictions of the civilized world, such wastes can no longer be put into the conventional channels of waste disposal. Nor can much of such wastes be reliably rendered safe and unrecognizable in a practical, discernible way at the point of use. On-site sterilization, by autoclaving, for example, of medical waste does not solve the problem because sterilization is not only labor-intensive, but subject to human error and all but impossible to verify. Also, sterilizing does not change the inherently dangerous character of sharps such as needles and scalpels, nor does it render syringe bodies unrecognizable or unusable Used hypodermic syringes are possibly the most dreaded waste of all because they are contaminated, dangerous to handle, resist decay, can float until a shore is found, and, as operative devices, are sought by the illicit drug trade. Until recently, medical facilities were required to shear off the needle part from the syringe body immediately after the injection, but this procedure was found to spread disease by means of the airborne aerosols generated by the mechanical shearing action. Also, the sharp, contaminated needle tip remained to be handled and disposed of. Current regulations call for dropping the contaminated syringe with needle intact into a safe container, called a "sharps" box, for custom delivery to an authorized repository in a costly and dubious process known as tracking A state-of-the-art device destroys the needle at the point of use by passing a large current at low voltage through the needle to reduce it and all attendant contaminants at temperatures of incandescence to a minute, sterile, incinerated residue That invention protects the nearby medical personnel and the environment but it cannot cope with scalpels, glass or the leftover hollow barrels of the syringes Thus, the medical facility, while performing a useful service to protect its personnel and society, is left with its other contaminated "sharps" and syringe bodies to ship to a safe repository. For its otherwise worthwhile efforts, it has saved little time and little, if any, total disposal cost.

There are also in the prior art techniques for rendering sharp items less dangerous by potting in gels, hardenable resins or thermoplastics. U.S. Pat. No. 4,662,516 to Baker Sr. et al., discloses a sharps waste collection box and an unverifiable sterilizing cycle in which the wastes are first caught in a thermoplastic bag and then placed in an autoclave to be processed through a conventional autoclaving cycle, i.e. steam under pressure for a timed interval, typically 20–30 minutes at approximately 120° C. The plastic bag and panels are shown to have melted at the autoclave temperature and are shown encapsulating at least to some extent the medical waste (a hypodermic syringe barrel and needle).

The finished product, however, remains hazardous by all applicable definitions and must therefore be handled as if it had never been treated. First, the treated waste is recognizable. Much of today's medical wastes, hollow syringe needles and barrels in particular, are buoyant in liquefied plastic; needles will in the absence of constraint project from the solidified mass making them not only recognizable but exposed and legally regulatable (even if actually sterile) The treated waste, however, is not sterile. Autoclave sterilization depends on "wet" heat reaching all microbial life for a finite period of time; shielding the waste in a plastic bag or immersing it in liquefied plastic defeats the wet or autoclave process. Thus, even more time and higher temperatures would be indicated if sterilization were to be achieved But more important, sterilization even if performed to all applicable standards is simply not verifiable on casual (or even less casual) inspection and better, safer solutions are sought.

The present regulations for dealing with medical instrument wastes not destroyable safely or rendered non-hazardous on the site call for: 1) minimum handling at the point of use, that is the person performing the injection, for example, is expected to drop the used syringe directly into the "sharps" box; 2) containerizing the waste by means of sealed and clearly marked and regulated waste containers, and 3) logging and shipping the containerized, contaminated waste to a special repository (typically a special state-of-the-art incineration station) under an umbrella of costly manifests which must circulate among the facility, the hauler and the repository and then kept available audit for several years. The expense of this tracking procedure to society is enormous and the beaches and land fills of the world reveal the flaws in the system.

The present invention is a fresh attempt to solve the problems Its objects and features are:

to provide a relatively inexpensive waste disposal container to receive the medical waste at the point of use;

to provide a way to process and sterilize inexpensively and verifiably the contaminated contents within the container while still at the medical facility, to render the syringe bodies in the container not only unusable but unidentifiable, and unretrievable;

to render the needles, the scalpels and the glass harmless against cutting or piercing personnel and to render them unrecoverable by any practical means;

to provide a containerized sterilizing system which is reliable and virtually immune to human error;

to provide a containerized sterilizing system which provides a biological indicator even to the casual observer whether the contents have been rendered harmless and safe;

to provide a containerized medical implement waste disposal system in which the treated container and its contents do not float;

to provide a reliable, relatively inexpensive method and apparatus to pretreat partial loads of medical wastes at the point of use on a day-by-day or even-on-demand basis in a manner which renders the contents unrecognizable, unusable and at least partially sterile, followed by a final sterilizing and encapsulating cycle to yield a product which can be thrown out in the ordinary channels of waste disposal; and to provide a containerized sterilizing system for medical implement waste which, if desired, lends itself to recycling.

BRIEF SUMMARY OF THE INVENTION

In accordance with the invention, a waste disposal container which can be similar in size and shape to existing "sharps" boxes is formed of a material such as metal or engineered plastic having a melting point exceeding sterilization temperatures. The container includes a temperature-calibrated or indexed-thermoplastic compound preferably having a melting temperature selected at a value at which sterilization of biological contamination is effected virtually upon contact. Used medical implement and general waste such as hypodermic needles, scalpels, tongue depressors, glass vials, tubing and hypodermic syringes, with or without the needles, as well as blood soaked gauze, extracted teeth or the like are accumulated in the container in the conventional manner. The full container is heated by appropriate means such as an oven to a temperature at or above the melting point of the temperature-calibrated compound When the compound liquefies, pressure is applied by a movable member to cause the hot liquid to flow into the space containing the then pre-heated waste products, to flow over and around all bits and pieces, and to fill substantially all void spaces between and in the waste items. The container is vented at the top and the flow continued preferably until the liquefied compound appears at or around the movable member. All biological life will then, or shortly thereafter, be killed as the liquid hardens with attendant heat of fusion effects.

In one embodiment, the container is partially collapsible to apply pressure Alternatively, the container can be formed of telescoping parts. It is this feature which provides an error-free, highly conspicuous and verifiable indication that the sterilizing and encapsulating steps have occurred within The pressure and containment of the compressed container forces all waste into the molten material and molten material into the void spaces. If desired, the outside of the container can be color and word coded to show the hazardous mode before the container is reduced in size and the safe mode thereafter.

The container is held in its new geometry until the compound has cooled and hardened to encapsulate and shield all sharp points and edges and to lock the container in its new geometry. The plastic of which disposable syringe bodies are made, having a melting temperature substantially below that of the compound, will be reduced to an amorphous, unrecognizable, void-free mass. Thus, there are no visually identifiable or usable syringe parts remaining in the final mass. The container is now hazard-free and can be disposed of in the conventional channels of waste disposal either at a land fill or an incinerator. It is also capable of recycling to retrieve the compound and the metals of which the medical implements were made, should such be desirable for any reason.

In another preferred embodiment of the invention, two or more differently temperature-calibrated (high and low) media can be used in the waste disposal container to effect economies of space and capacity and to make it possible to pre-treat and render at least partially safe a plurality of successive small loadings of hazardous waste on a day-by-day or even hour-by-hour basis. As above, the container is locked in its full open, hazard-indicating geometry by a volume of high or sterilizing temperature medium. Additional low melting point medium can be embodied in the inside container design or added as a supplement in the form of loose material, secondary plastic sharps containers or by plastic medical waste items per se.

Design considerations are discussed in greater detail below but in brief medical waste items which are non-meltable and non-compressible such as glass anesthetic and blood vials, extracted teeth and metal implements are at one end of the displacement spectrum and meltable and compressible items such as plastic syringe barrels, flexible tubing, sharps boxes and blood soaked gauze are at the other. The invention addresses both extremes and the gamut of combinations.

In the previously described embodiments, a fully waste-loaded container calls for a finishing and sterilizing cycle which ends the processing life of the basic medical waste disposal container. In this embodiment, the two differently temperature-calibrated plastic media matched by a companion oven having two processing temperatures enables initial full charges of waste to be preliminarily processed reducing their volume significantly (with substantial safety benefits) without triggering the final action Successive loadings, although progressively smaller in volume, materially augment the total capacity of each processing container, e.g. a 100 fl. oz. capacity container can process up to approximately 400 fl. oz. (displacement) of meltable compressibles and up to 200 fl. oz. of non-compressibles; the cost savings are substantial.

The pre-processed materials will be rendered unrecognizable, unspillable, essentially unusable, substantially free of biologically active materials (and therefore odor-free) and, to a very large extent, sterile. But for the projecting sharps or hazards, all disposed, however, within the closed container (preferably also housed within its oven) and but for resistant spores, the intermediate or preliminary treatment has rendered the waste safe. Smaller charges of known highly dangerous waste can be immediately processed at any time and a day's collection can be processed even if less than a full charge, all without triggering the final sterilizing step which necessarily ends the useful life of the waste-processing container.

When, however, the container does reach its ultimate capacity which can be either visually or mechanically signalled to the waste generating facility, the final sterilizing and finishing stage with an oven-temperature of say 190° C. or above is initiated. The mass is rendered totally biologically inert, all projecting needles (hazards) within the container are submerged by compression, there are no recognizable or re-usable, elements and the container reverts from its hazard-indicating mode (by warning indicia on a surface) to non-hazardous in every way (including obliterating the warning indicia) for disposal in the regular waste channels. In accordance with the invention, supplemental forces can be applied by the oven to assist in the compression stage and various safety interlocks, automatic cycling and load weighing features can be added to the oven and container functions.

DESCRIPTION OF THE PREFERRED EMBODIMENTS

Referring to FIGS. 1-4, the invention is illustrated as embodied in a container 10 formed of a heat and puncture resistant material such as engineered high melting point plastic, of which nylon and teflon are examples and which can be reinforced, or of metal. The container 10 is cylindrical and includes a rigid upper portion 11 defining a chamber or space 12 to receive waste implements such as hypodermic needles, glass vials, scalpels, extracted teeth and like waste products which in the medical and dental professions are now known as contaminated "sharps". Syringe bodies, with or without the needles attached, flexible tubing and needle hubs can also be included, such typically being of the single-use, disposable type formed of thermoplastic. Such thermoplastics typically melt at temperatures ranging up to approximately 150° C. so that all thermoplastic waste items will be melted down and rendered unusable, unretrievable and unrecognizable. The upper portion 13 of the container is preferably convergent to form a relatively small waste-receiving opening 14 having a depending cylindrical wall 15 and closed by a detachable vented cap 16.

The lower or base portion of the container comprises a collapsible storage space 18 containing a thermoplastic medium 19 which is temperature calibrated as to its melting point selected to achieve sterilization of all known biological micro-organisms including vegetative bacteria, viruses and spore forms. A typical material for this purpose which is relatively harmless to the environment is linear, hydroxy terminated copolyester synthetic resin which can be formulated to afford full flow viscosity at temperatures from 160° C. to in excess of 260° C. Such products do not vaporize or generate toxic fumes until temperature in excess of 300° C. are reached. They are marketed for other purposes under such trademarks as Dynapol and Jet-Melt Many acrylics can also be adapted for the purpose.

Most medical researchers studying the effects of heat as a means of sterilizing refer to a temperature co-efficient model in which death of the micro-organisms being studied (death time) is plotted as a function of time and temperature Research strongly indicates that no known micro-organisms can survive temperatures in excess of 160 to 190° C. for longer than a fraction of a minute. See "Disinfection, Sterilization and Preservation", by Seymour S. Block, Lea & Febiger, 1983. It should be understood, however, that there is a given range of times and temperatures below 160 to 190° C. which effectively kill all known micro-organisms. It is, therefore, possible to design systems whereby plastics having melting temperatures less than 160 to 190° C. are allowed to remain in contact with the micro-organisms for times consistent with the death times of the organisms. The preferred embodiment, however, makes use of plastics having temperatures high enough to kill the micro-organisms substantially on contact, and, thereby, provides a fail-safe degree of overkill. Also, the system of the present invention provides an inherent time constant representing the time for the liquid phase thermoplastic to revert during cooling to its solid final phase, yielding heat of fusion without requiring a timing function subject to human error.

In dry gaseous media such as hot air having relatively lower specific heat characteristics and little moisture, either higher temperatures or measurable time constants for heat exposure come into play. In the preferred embodiments of the present invention, liquid phase contact at temperatures achieving rapid death to all biological contaminants in their most heat-resistant form, i.e. the spore form, is desirable because it eliminates the possibility of human error in the operation of the system and renders the successful operation visually discernible and, therefore, verifiable at a glance from a substantial distance, all of which are vital in policing the environment for human life-endangering contamination.

The appearance of the thermoplastic material at the vented cap will indicate that the entire space 12 has been impregnated with molten plastic To provide for the possibility that the displacement factor of the waste items in the space 12 will have a range of values, a surplus of thermoplastic can be provided together with an overflow reservoir 13a in the form for example of a visible, open cup surrounding the cap. To accommodate a situation in which the waste items 17 only partially fill the space 12, the conical upper portion 13 can be made collapsible under pressure in the encapsulating phase as described below.

The temperature-calibrated thermoplastic medium 19 in the embodiment of FIGS. 1–4 is illustrated as solid although it can take the form of particulate matter or granules including recycled plastics To hold the granules in place prior to melting a covering screen, a perforate cover (not shown) can be secured to the container above the material.

The wall of the base portion 18 of the container is made collapsible by corrugation or accordion pleating locked in its open position (FIGS. 1 and 3) by the solid phase of the thermoplastic medium 19 and also locked in its collapsed position (FIGS. 2 and 4) by the same medium. If it is desired to make the container self-actuating (in the presence of heat), the collapsible wall can be made resilient with its stable or rest position collapsed. To this end, a coiled tension spring (similar to the spring 37 in FIGS. 5 and 6) can be included inside or outside the container if additional force is required. Additional force can also be derived from the use of heat shrinkable plastic in the container walls either on the x or the y axis or both, or it can be derived in whole or in part by the oven.

Figure 9:
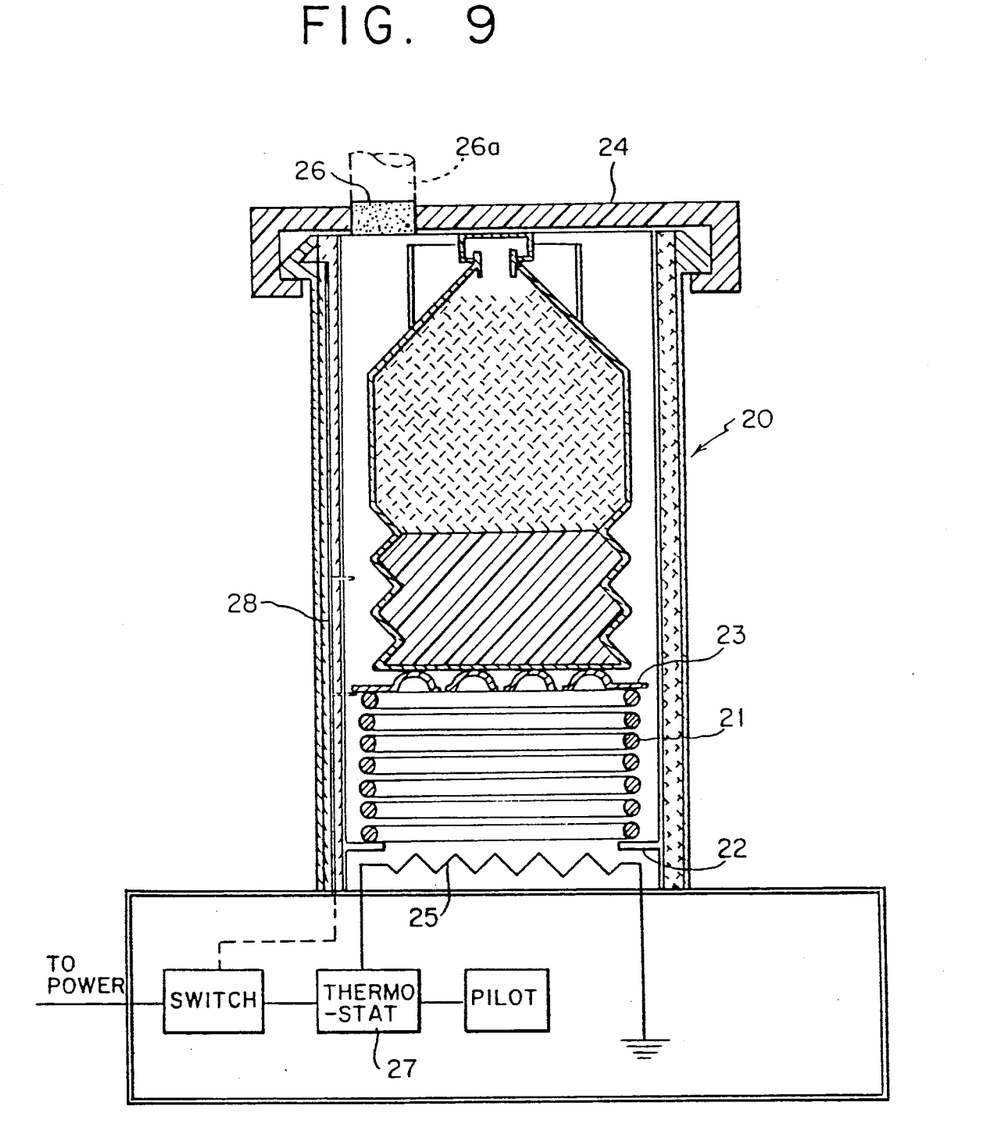
FIG. 9 is a view in vertical section of an oven containing a filled container corresponding to that of FIG. 3 and capable of carrying out the sterilizing and encapsulating functions.
Figure 10:
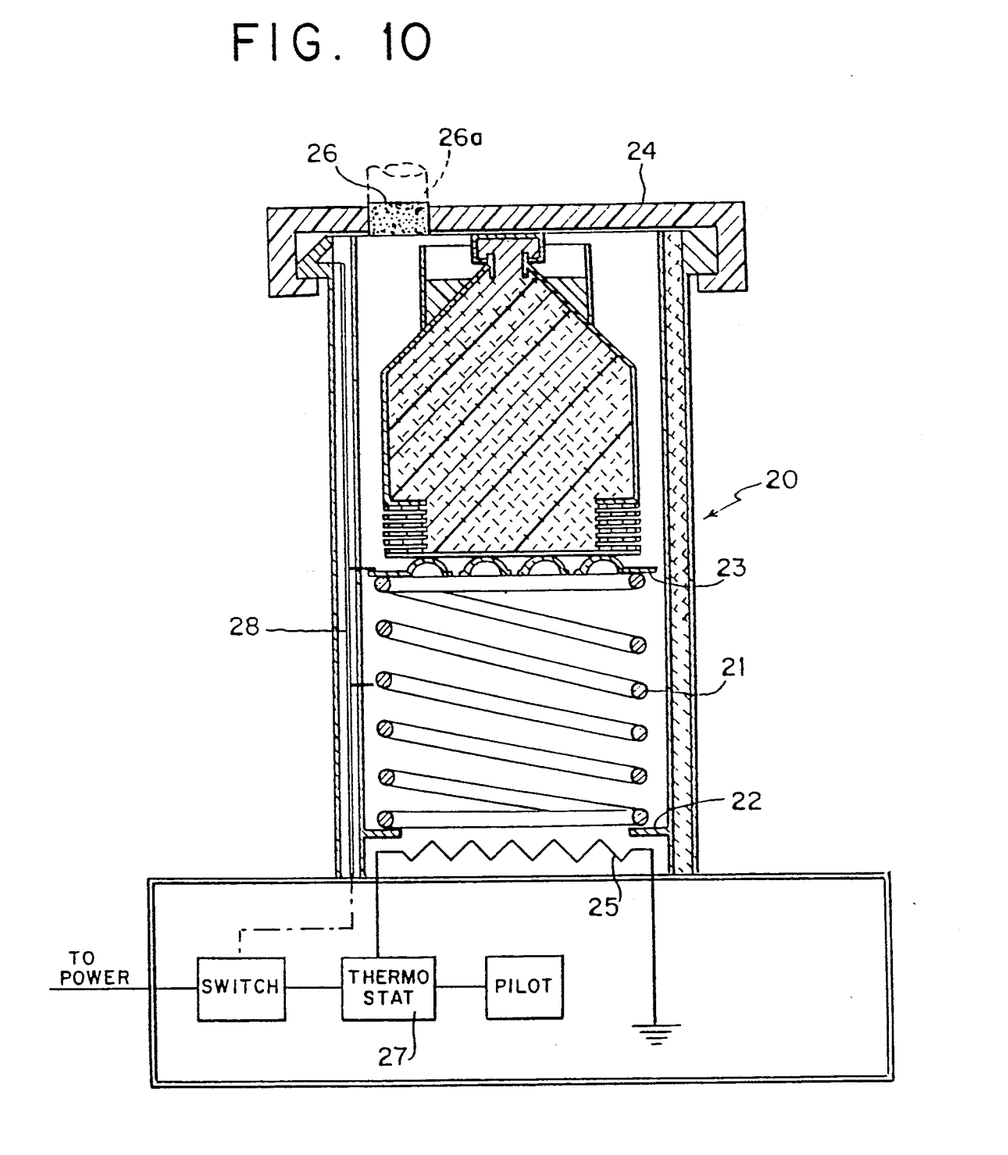
FIG. 10 is a view in vertical section of the oven corresponding to FIG. 9 but showing the container after sterilization and encapsulation.

The sterilizing and encapsulating actions in the illustrated embodiment are carried out by a special oven 20 shown in FIGS. 9 and 10 which provides forces necessary to compress the container. The oven 20 includes a compression spring 21 resting on a support 22 and carrying a perforated, corrugated plate 23 on which the filled container 10 (FIGS. 1 and 3) is seated. The spring 21 is compressed by the closed oven cover 24 pressing down on the container cap 16. A resistance heater 25 energized from the mains through a switch and thermostat 27 provides the controlled heat to liqufy the temperature-calibrated thermoplastic mass 19. As heat is applied, below the level to harm the container and above the level to liquefy the thermoplastic, melting will gradually occur at which time the liquefied thermoplastic at a temperature pre-selected to destroy the biological contaminants in the waste items 17 will begin to flow into the interstices around the preheated bits and pieces of waste in the space 12.

The biological contaminants are destroyed substantially upon contact and all sharp edges and points become encapsulated. Also, the collapsible bottom 18 of the container will compress, thereby changing the geometry and appearance of the container. Gaseous byproducts vent from the cap 16 and through a suitable filter 26, including charcoal, for example, in the cover 24 of the oven and, if desired, an evacuation conduit 26a. Alternatively, or in addition, the oven can be vented to the outside air, as is conventional in autoclave operation. The cooled container is thus rendered hazard-free and can be discarded in the conventional channels of commerce by conventional carriers Thermoplastic syringe bodies in the container melt at temperatures below the calibrated temperature and are, therefore, melted down and destroyed as an unusable, irretrievable, unrecognizable part of the sterile, amorphous mass.

The oven 20 can be operated by a position sensing switch actuator 28 which is activated by the carrier plate 23 to initiate heating when the plate is lowered and to terminate heating when it lifts (FIGS. 9 and 10). The actuator can also be coupled to the cover 24 to release a latch when the heating cycle is completed. The cover can be spring biased to an open position when released to hurry the cooling cycle, and residual compression in the spring 21 can expose more of the container to the atmosphere and also position it to be more easily manually removed.

Figure 1:
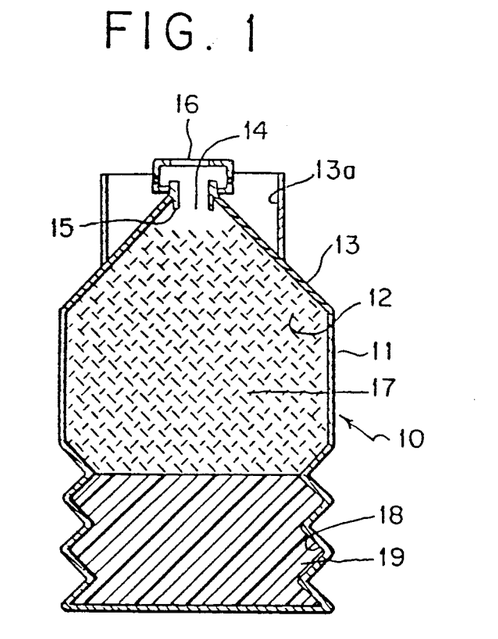
FIG. 1 is a view in side view in vertical section of a waste container formed in accordance with the invention holding a charge of medical waste prior to the sterilization and encapsulating steps.
Figure 2:
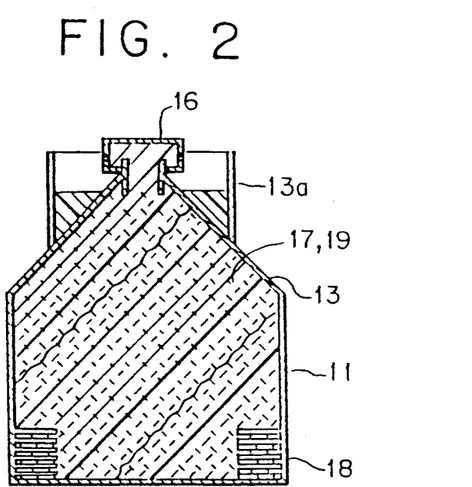
FIG. 2 is a view in side view in vertical section corresponding to FIG. 1 after the sterilizing and encapsulating steps; 0
Figure 3:
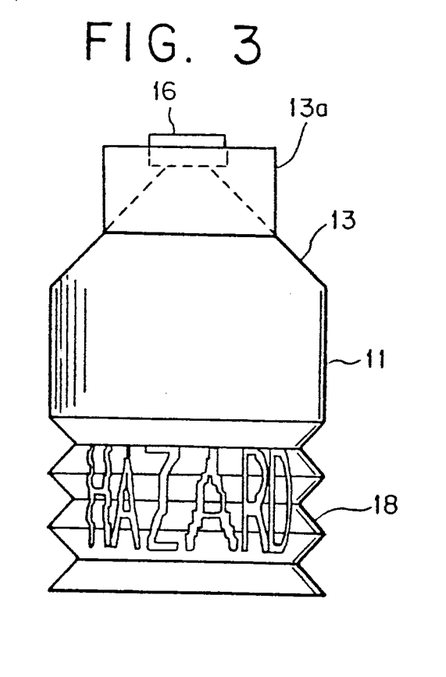
FIG. 3 is a view in side elevation of the waste container shown in FIG. 1.
Figure 4:
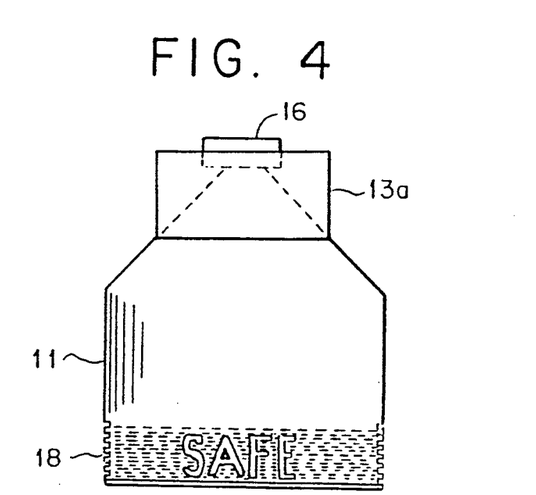
FIG. 4 is a view in side elevation of the waste container shown in FIG. 2, after sterilization and encapsulation of the waste.

The thermoplastic mass, when cooled, locks the container in its compressed condition to mark its sterile non-hazardous condition. If desired, as best seen in FIGS. 3 and 4, the concave or depressed portions of the base can be color coded in red to indicate the hazardous state and a word to that effect can be included. The word "Hazard" as used in this disclosure is intended in its broader sense to mean contaminated, sharp or infected and not, for example, explosive or highly inflammable. "Regulated medical waste" is a more precise legal definition of the waste to which this invention is directed. The outer edges can be marked so that when compression has occurred the word "safe" appears and the hazard indicator disappears. Because the thermoplastic mass 19 has been selected for a melting temperature close to or above that which sterilizes on contact, the system becomes error proof and visually verifiable. It will be understood that a certain margin for error is built into the system in that a finite time factor for killing by heat is inherent in the system representing the time for cooling down to the solid phase with attendant heat of fusion. Thus, it is not essential that the temperature of the liquefied thermoplastic actually reach that which kills instantaneously, although it is preferred where possible to establish safety factors using both elevated temperatures as well as any time factor which is inherent in the time required for the temperature of the thermoplastic to drop to that at which the solid phase occurs.

Figure 5:
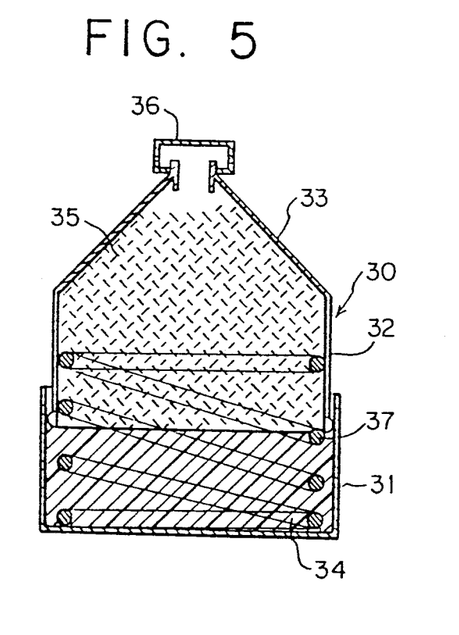
FIG. 5 is a view in vertical section of another embodiment of the invention prior to sterilization and encapsulation.
Figure 6:
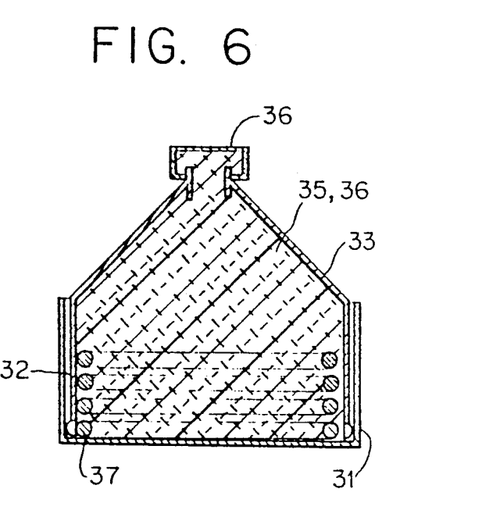
FIG. 6 is a view in side elevation of the unit of FIG. 5 after sterilization and encapsulation.

Referring to FIGS. 5 and 6 another embodiment of the container is disclosed in which the container 30 is formed of telescoping base and top sections 31 and 32, respectively. As in the embodiment of FIGS. 1-4, the upper part 33 of the top section 32 is conical. Normally solid phase thermoplastic 34 fills the base 31 with waste items 35 filling the upper section, shown closed by a vented cover 36. The thermoplastic 34 can bond the base and top sections 31 and 32 against opening to retrieve unprocessed waste items such as syringes. If desired, the two telescoping sections can be linked by a coiled tension spring 37 joined at its top to the section 32 and its bottom to the base section 31. The container is adapted to be placed in an oven similar to that of FIGS. 9 and 10 to liquefy the thermoplastic and thereby set up the sterilizing and encapsulating functions, resulting in the configuration of FIG. 6 under the spring force, gravity or a combination thereof. Hazard warnings in the cylindrical part of the upper section will, appropriately, be obscured by the lower section. It will be understood that heat destroyable warnings can also be used.

Figure 7:
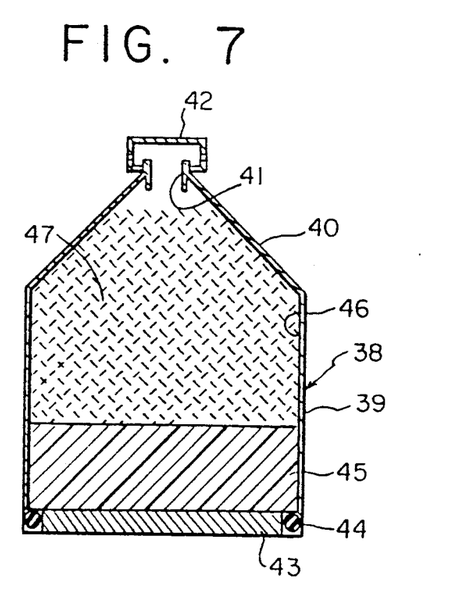
FIGS. 7 and 8 are views corresponding to FIGS. 5 and 6 of another embodiment of the invention.
Figure 8:
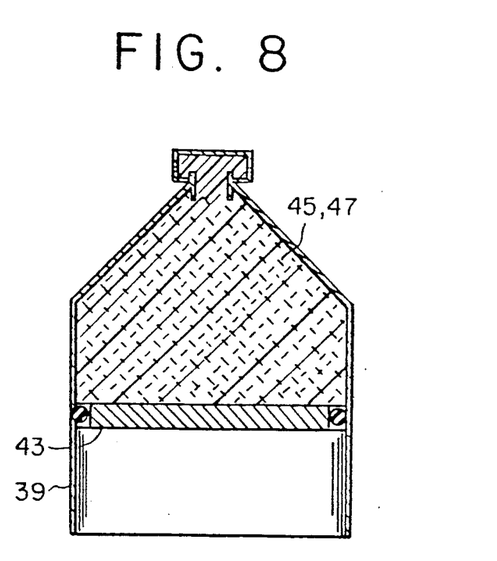

Referring to FIGS. 7 and 8 another embodiment of the invention is disclosed in which the container 38 is formed of a single piece having a cylindrical bottom 39 and conical top 40 with a filling opening 41 shown closed by a vented cover 42. The bottom portion 39 is open and has fitted thereon a piston 43 with a sealing ring 44. The bottom is filled with a volume of thermoplastic 45 of the type described above and the open space 46 above is shown filled (diagrammatically) with an array of waste items 47. A tension spring or other internal or external pressure means corresponding, for example, to the spring 37 of FIGS. 5 and 6 can be used. The filled container is then heated by, for example, an oven corresponding to that of FIGS. 9 and 10 to drive the liquefied thermoplastic into the waste items, all as described above, to achieve the end result shown in FIG. 8.

Figures 11, 12:
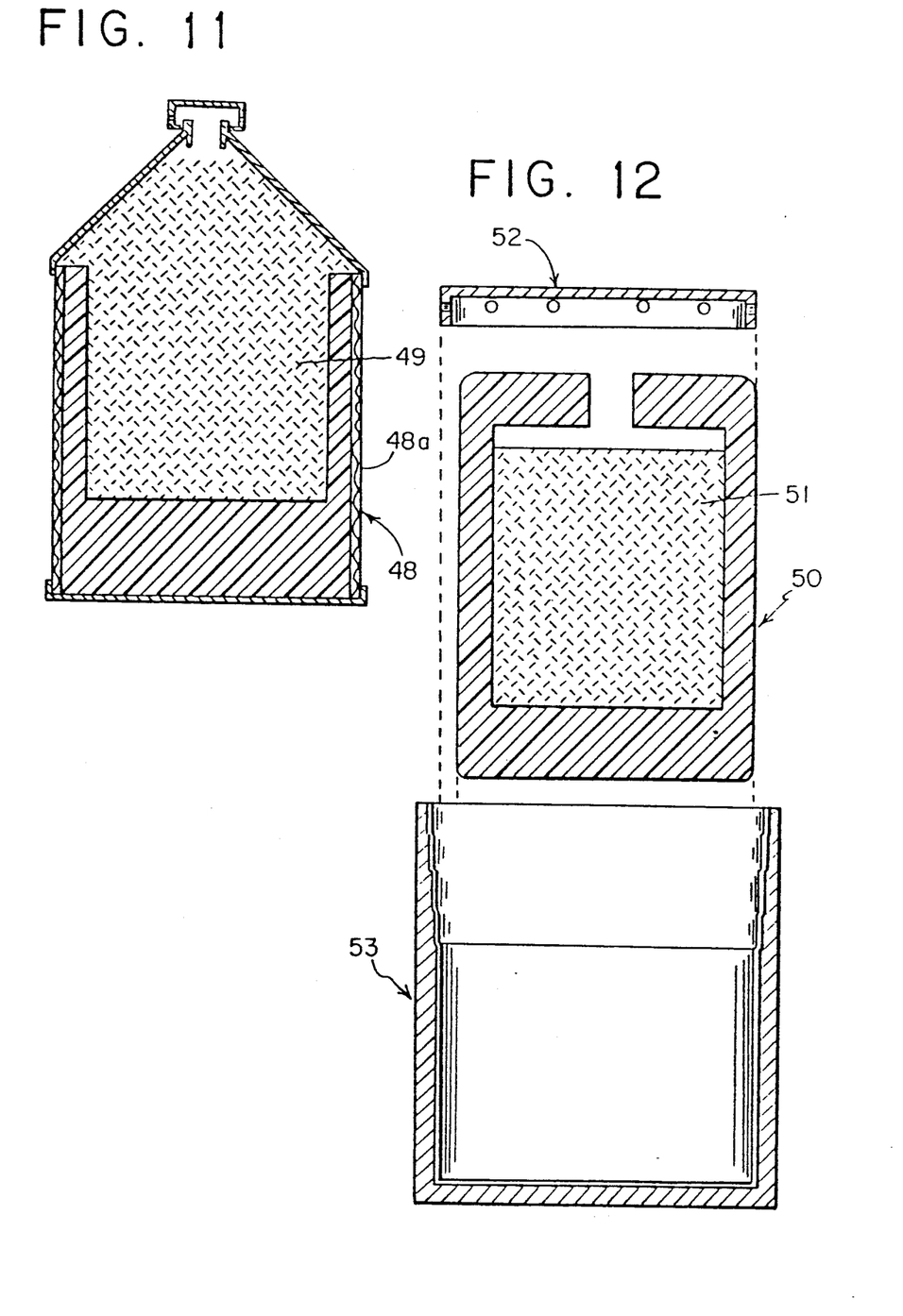
FIG. 11 is a view in vertical section of another embodiment of the invention.
FIG. 12 is a view in vertical section showing another embodiment of the invention using a separate potting container.

Another embodiment of the invention is shown in FIG. 11 in which the container 48 is itself formed of the temperature-calibrated thermoplastic resin having a wall volume corresponding to the volume required to impregnate and encapsulate the waste items 49 contained therein. The container 48 can be encased in a wrap 48a of woven or non woven filaments or of paperboard to contain and shield the liquid phase of the thermoplastic and the waste items 49. The wrap can impart deformability to the structure either in selected areas or throughout to allow the liquefied thermoplastic to be forced into the waste mass and, if desired, to adjust the container volume automatically to accommodate loads of different sizes and having different displacement characteristics. The wrap can be made puncture proof. It can also establish the pattern of change in the geometry between the treated and untreated unit to provide for the desirable visual verification of completion of sterilization.

Referring to FIG. 12 the entire sharps container 50 is formed from temperature-calibrated thermoplastic with no outer wrap or outer container. When filled with waste items 51 the container 50 with a vented cover 52, which can if desired be weighted, is dropped into a potting container 53 having tapering walls with a smooth parting surface formed for example of Teflon. The assembly is then heated in an oven to melt the thermoplastic container 50 to a sterilizing temperature of liquefaction at which time the gravity pressure causes encapsulation and impregnation of the waste items 51. When cooled and solidified the amorphous sterile mass with no projecting needles or sharps is removed from the potting container 53 for disposal as environmentally safe material via conventional disposal means.

It will be understood that while the embodiments of the invention described above utilize, as the bulk of the thermoplastic content of the containers, a temperature-calibrated thermoplastic having a melting temperature selected to achieve the desired extreme of verifiable sterilization, lower melting temperature plastic can be included within the scope of the invention to achieve additional functions. To the extent, for example, that the medical waste is itself formed of thermoplastic, such as syringe bodies, flexible tubing, scalpel handles, needle hubs and the like, lesser volumes of high temperature-calibrated thermoplastic will be required to effect total encapsulation of and therefore lack of recognition of all waste items. It is also possible to combine volumes of low and high melting temperature thermoplastic in the initial container design because the high temperature material will compel and therefore verify that the low temperature material has, in fact, while liquefied at a low temperature been raised to a temperature which is above both its actual melting and full flow liquefaction temperatures. This feature can be used to advantage to achieve in the operating container full flow (or low viscosity) characteristics in the material which can contribute to a relatively void-free structure in the finished product.

Referring to FIGS. 13-17 there are disclosed embodiments of the invention which provide maximum space utilization within the waste disposal container while providing for a large number of preliminary treatment cycles which can destroy, render unusable, and at least partially sterilize either large or small amounts of medical waste on demand The final total-sterilization, pressure-encapsulation, and container geometry-changing cycle, all as broadly described above, can await the accumulation of waste materials approaching the theoretical maximum capacity of the container To achieve these functions, in accordance with the invention two temperature-calibrated thermoplastic elements in the form of concentric sleeves 54 and 55 (FIG. 13) are fitted within a metal container 56. A removable cover 57 provides a large opening for depositing wastes in large or small amounts into the container, which can have a relatively large capacity, for example 100 fl. oz. of displacement (up to a month's capacity for smaller medical waste generators). Preliminary treatment significantly increases the safe working life of the unit.

Figure 13:
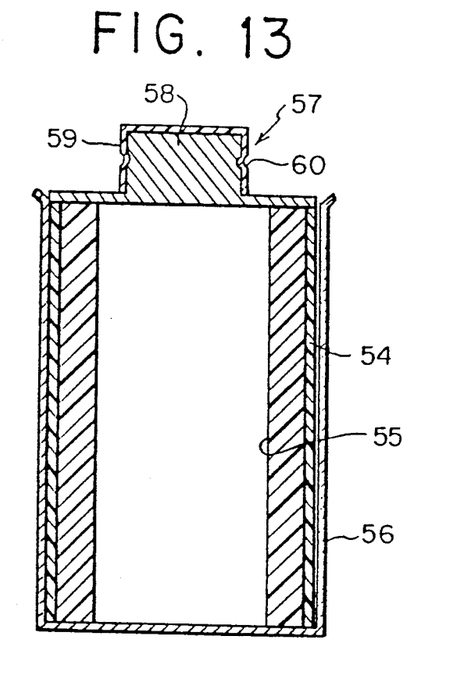
FIG. 13 is a view in vertical section showing another embodiment of the invention.

The cover 57 comprises the movable compression member of the unit and includes an upstanding cylindrical center portion 58 serving as a gripping handle and providing an outer cylindrical surface 59 to carry the graphics warning of the hazardous contents The center portion 58 can also be weighted to assist in the final compression cycle. A groove 60 can be provided for automatic gripping by an oven component for automated lifting, all as described below referring to FIGS. 16 and 17.

The melting temperatures of the two concentric sleeves 54 and 55 are critical to this embodiment of the invention, the sleeve 54 being calibrated at the high melting valve, 160 to 200° C., which gates the final desired sterilization temperature of the waste mass. The sleeve 55 is calibrated at a lower melting temperature, 110 to 150° C., to effect preliminary treatment, destruction and at least some sterilization and loss of recognition at least some of the of medical wastes on demand in recurring cycles.

The volume and geometry of the high melting point plastic 54 is selected to stabilize the cover against compression movement except when the selected high temperature for final treatment is commanded by the oven. The volume of the low temperature thermoplastic 55 is selected to effect full encapsulation of the waste, obliteration of the hazard graphics, and sealing of the compression cover 57. If the waste container is to be universal in its utility it must accommodate on the one hand incompressible wastes such as glass anesthetic and blood vials, needles, scalpels, extracted teeth, and the like (which en masse, as well as individually, present void spaces) and, on the other hand, compressible and meltable wastes such as thermoplastic syringe bodies, flexible tubing, scalpel handles, (which themselves undergo substantial volumetric reduction when they melt down, at the same time adding volume to the total thermoplastic mass needed in the container.

Assuming the container 56 has a capacity of 100 fl. oz., the sleeve 55 (following design criteria set forth below) would have a total displacement of 50 fl. oz. Thus, the container presents a 50 fl. oz. space (within sleeve 55) for its initial charge of wastes. Measurements show that incompressible medical wastes of the type described filling a 50 fl. oz. space contain about 25 fl. oz.

of void spaces. If, therefore, the container is placed in its 2-temperature oven (FIGS. 16 and 17) and operated at the temperature required to liquefy the sleeve 55 to full flow conditions, the mass of waste will "consume" 25 fl. oz. of the plastic and thus generate more usable volume. The inside usable container space will change from a narrow cylinder to a wide cylinder as the plastic sleeve 55 melts and the impregnated mostly encapsulated waste mass will occupy the lower half of the container (ignoring for discussion purposes the thin sleeve 54) plus an additional 25%, which represents available encapsulating plastic for on-going waste loads. Successive loadings, necessarily proportionately smaller in size will eventually exhaust the system at a point approaching but typically not quite achieving theoretical maximum capacity (100 fl. oz.). Of course the preliminary treating operation can be performed at any time without the then available space having been filled, as when a particularly dangerous small waste charge is entered or when the facility closes down for the night.

Next, consider the empty container as receiving only thermoplastic medical waste items. Measurements shows a selection of such items typically melts down to about one-forth of the space it occupies. If therefore such wastes fill the space of the container configuration as shown in FIG. 13 there will be a volume of waste consuming 50 fl. oz. of space. Melted this will reduce to about 12.5 fl. oz. of thermoplastic. In such a hypothetical case the sleeve 55 will perform no function; it is essentially for "sharps" protection. It is preferred, however, that both it and the oven be calibrated to effect the preliminary melt down at a temperature which is sufficiently high to ensure that thermoplastic medical wastes such as syringe bodies are destroyed by melting to ensure safety and economy of space. Medical thermoplastic wastes characteristically liquefy at temperatures below 140° C. It is the glass vials for anesthetics and blood (categorized as "sharps") which require the added mass of thermoplastic, whether it be of the high or low melting temperature.

Another criterion in the equation is to avoid vapor point temperatures for all thermoplastics involved, typically above 215° C. for plastic materials used in medical implements. Such vapors can be toxic, but it is possible to achieve all important objectives of the invention operating substantially below that limit.

Figure 14:
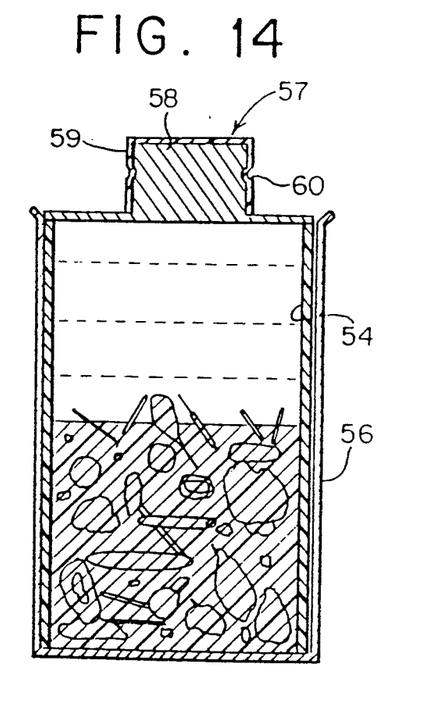
FIG. 14 is a view in vertical section of the medical waste container of FIG. 13 showing a full loading of random medical wastes pre-treated at the lower of two treating temperatures.

As stated, preliminary processing can be carried out in the unit in any number of stages until total operating capacity is approached. FIG. 14, for example, illustrates a preliminary processing of at least one full loading of medical wastes including compressible and non-compressible wastes. The dotted level lines show possible successive waste levels treated preliminarily. The sleeve 54 survives as shown.

Figure 15:
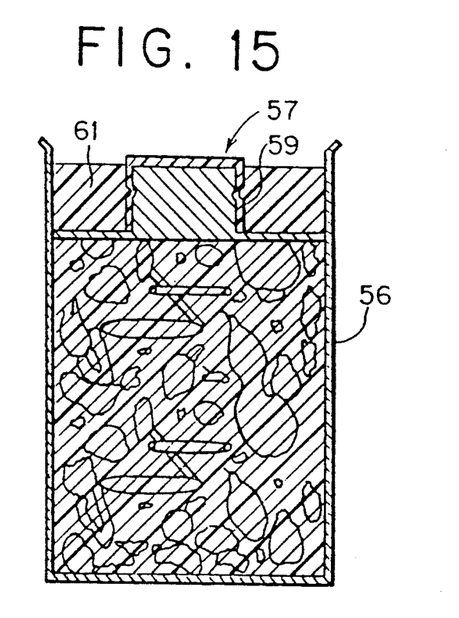
FIG. 15 is a view in vertical section showing the container after a plurality of pre-treated loadings to approximately full ultimate capacity and also after the final high temperature sterilization and compacting cycle to seal the cover portion in place over the substantially void-free structure.

FIG. 15 illustrates the effects of the final processing in which the oven has been operated at its maximum temperature to melt down the outer sleeve 54, release the compression cover 57, and submerge all non-compressible sharps hazards beneath the plastic mass (a mixture of sleeves 54-55 and the meltable thermoplastic components in the medical wastes). The cover 57 is vented by providing, for example, a small radial clearance with the wall of the metal container 56 to allow gases to escape as well as sinking of the cover into the plastic mass and the appearance of plastic in the reservoir space between the side wall 59 of the cover extension 58 and the inside of the container 56. This obliterates the hazard graphics as well as locking the cover in place. The container, fully processed, is now free of hazards, biological and mechanical, and is believed harmless to the environment and safe in all hands for final disposal in any one of several ways including, if desired, recycling through the open mail.

Figure 16:
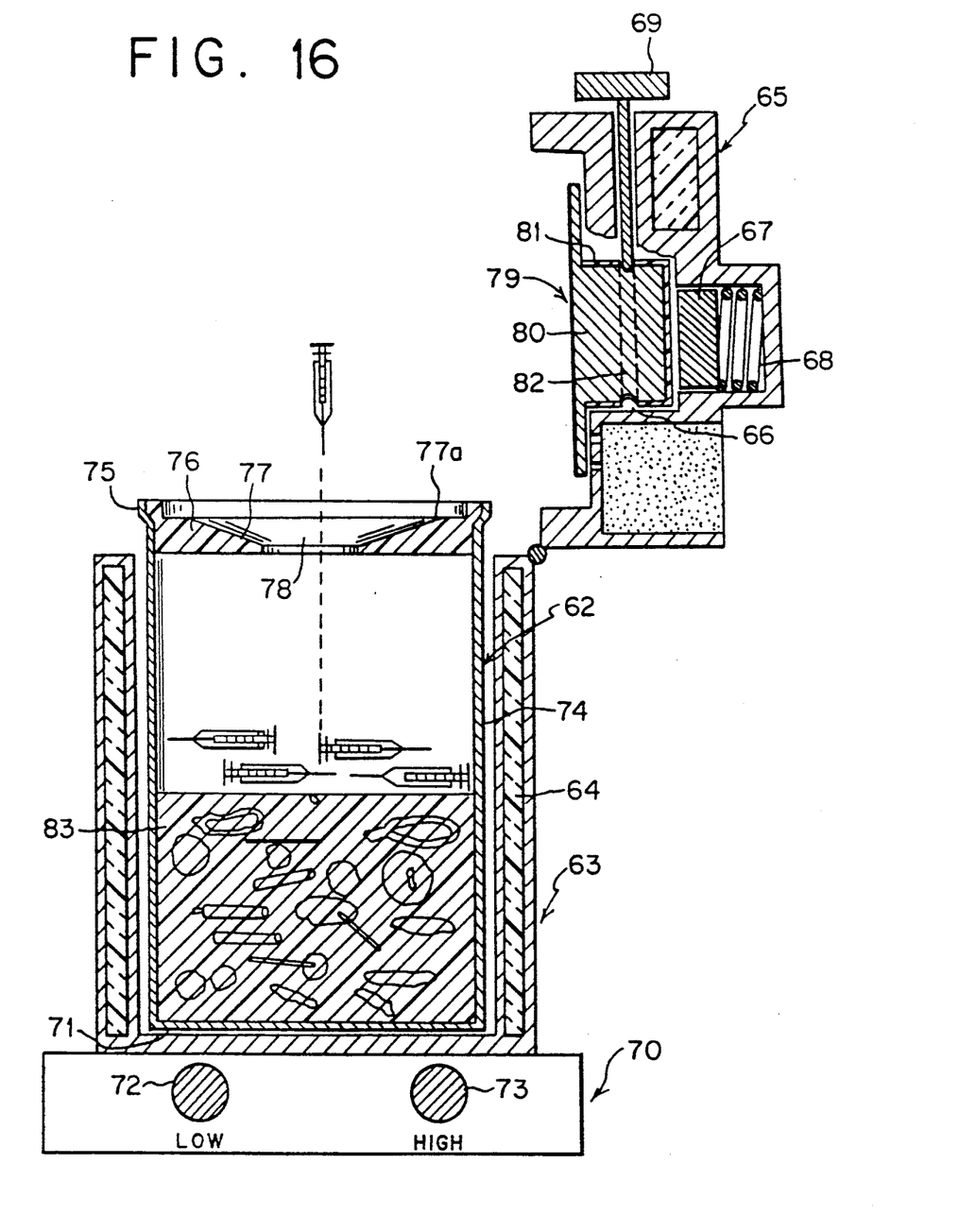
FIG. 16 is a view in vertical section of another embodiment of the invention shown in its treatment oven with its top cover carrying the removable cover of the container open to facilitate loading the container with waste items after at least one pre-treatment cycle.
Figure 17:
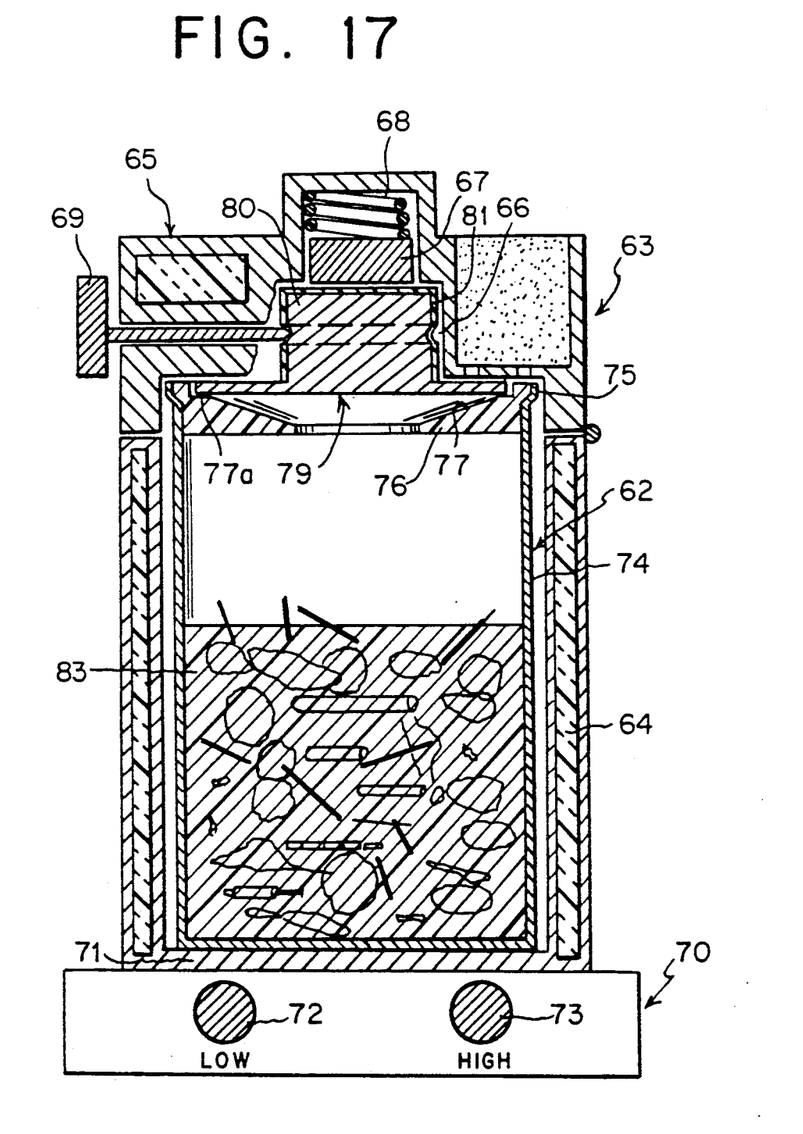
FIG. 17 is a view in vertical section corresponding to FIG. 16 but with the oven and container covers closed and after a second treatment cycle

Referring to FIGS. 16 and 17, there is illustrated another embodiment of the invention in which the medical waste container assembly 62 is seated in a 2-temperature treatment oven 63 (shown diagrammatically) comprising an insulated cylindrical wall 64 and a hinged, insulated cover 65. The cover includes a recess 66 to receive the cover of the waste container 62, a piston 67 driven by a compression spring 68 to bear down on the cover and a spring biased automatic latch 69 to grip the cover. The oven includes a base 70 which can contain an electrically heated plate 71 having 2 relatively precision operating temperatures, the lower being in the range, for example, of 110 to 150° C. and the upper of 160 to 200° C. Manual switches 72 and 73 can be provided to operate, respectively, the low and high temperature operations for whatever predetermined time intervals are indicated, say one hour more or less per cycle. Some or all of the oven function can be automated in accordance with well known techniques and the usual assortment of safety interlocks and the like provided to discourage tampering, improper use, or excessive temperatures.

The container unit 62 includes a metal cylindrical container 74 having a contoured upper edge 75 within which is seated a contoured insert 76 formed of a temperature-calibrated thermoplastic to soften and liquefy at relatively high temperature, say 160 to 200° C. Examples of such materials have been given above The calibrated insert 76 can include a gently downwardly converging wall 77 to a large central opening 78 through which medical wastes can be deposited into the unit. Other geometrical configurations for the temperature-calibrated insert 76 will suggest themselves to those skilled in the art.

A unit cover 79 (corresponding to the cover 57 of FIGS. 13-15) has an outside diameter slightly smaller than the diameter of the container 74 (for venting) and normally rests within a circular ridge 77a formed on the contoured insert 76. The central, upstanding portion 80 is engaged on its upper surface by the spring biased piston in the oven lid. Hazard graphics appear on its outer wall 81 and a circular groove 82 receives the releasable latch element 69 of the oven so that when the oven door is opened the cover 79 is automatically lifted from the waste container unit 62. Disposed within the waste container is a supply of thermoplastic 83 which is calibrated to liquefy at a relatively low temperature, say 110 to 150° C.

Preliminary or low temperature processing of medical waste proceeds as described above in recurring cycles of large or small charges of waste items. When ultimate capacity is reached the cycle is changed to high temperature, at which time the contoured insert 76 of temperature-calibrated thermoplastic melts, allowing the cover 79 to drop (by a combination of its own weight and the force of the spring 68) into the container 74 to compress the heated mass, obliterate the hazard graphics, change the container geometry and lock the cover, all as described above.

It will be understood that the geometry of the calibrated low temperature plastic mass 83 has been shown in FIGS. 16 and 17 simply as a cylindrical slug of solid material. It can, of course, take other forms such as a cylindrical sleeve or it can take the form of loose granules or recycled chips Its total volume is also subject to variation based on design and use factors. It should also be understood that because the function of the calibrated low melting temperature plastic is primarily associated with one particular type of medical waste i.e. non-compressible, non-meltable sharps of glass and metal, an alternative possible source of the supplemental thermoplastic, in accordance with the present invention, is the sub-containers in which the sharps are typically collected on the site of the waste generator. The volume of the calibrated thermoplastic used in fabricating the container (either by means of a special insert or by means of wall thickness) is keyed to the sharps capacity of the sub-container to provide an approximately correct amount to fill the void spaces and encapsulate the waste in the waste treatment container. In such event the entire filled sub-container, a sharps box in itself, is simply thrown into the waste container for preliminary processing, as opposed to being emptied into the waste process unit While the invention has been described having reference to preferred embodiments it will be understood that it can take other forms and arrangements. For example, the temperature-calibrated element can be formed of materials other than plastic, so long as the material in its molten state is compatible with the temperatures required in the time/temperature death rate curve and has appropriate liquid and solid phases. It is also important that the molten material be brought into intimate contact with the contaminated waste material In addition to the preferred embodiments herein disclosed it will be understood that this encapsulation can be augmented by rolling, tumbling, shaking, vibrating, and air evacuation devices. Partial evacuation of the container can perform the manifold functions of aspirating waste gases, augmenting the flow of the liquid-phase plastic into all voids and of providing some or even all of the compression forces to cause the distortion of the container. This distortion forces the liquid into the mass of waste implements and, at the same time, provides for the easily viewed indication of successful completion of the sterilizing cycle In the preferred embodiments the essential operational functions have been divided between the oven and the container. For example, the oven is the source of the controlled heat as well as the pressure, i.e. the spring 21, to extrude the liquefied sterilizing medium into the mass of waste pieces. As disclosed, some or all of this pressure can be generated solely within the container itself by, for example, the internal spring 37 (FIGS. 5 and 6), the resilience of the base 18 (FIGS. 1-4) or the heat shrinking forces of certain plastics. It will be understood that it is possible to generate heat by different means such as chemically within the container itself or by means of microwave energy focussed on the solid plastic, avoiding to the extent possible solid metal items. The plastic can be rendered more susceptible to such heating by means of carbon dielectric fillers. It is also possible to establish more of the functions externally of the container by, for example, generating the liquefied sterilizing medium externally and injecting it into the waste filled containers, which can be partially evacuated to augment the liquid flow to create a void-free mass and which can also provide a force to deform the container to provide a visual indication that the process has been completed. The invention should not, therefore, be regarded as limited except as defined in the following claims.

I claim:

1. Apparatus for receiving, sterilizing and encapsulating biologically contaminated wastes comprising
   a heat resistant container having a waste receiving space;
   a volume of a normally solid thermoplastic compound associated with the container and having a temperature-calibrated melting point;
   a movable container portion movable to cause the compound in it heated liquid phase to flow into and around the mass of waste in said space to effect verifiable biological sterilization and, upon hardening, encapsulation to the waste items in a unitary solid mass;
   means to hold the movable container portion in its inactive position through a plurality of successive loading and melting cycles; and
   selectively operatable means to release the movable portion.

2. Apparatus as set forth in claim 1 in which at least a portion of the temperature-calibrated thermoplastic compound has a melting point at a temperature corresponding substantially to that which destroys biological life including spore forms on relatively brief contact, whereby the operation of the apparatus is rendered substantially free of unverifiable time constants subject to human error.

3. Apparatus as set forth in claim 1, said container including externally visible means responsive to displacement of the movable portion of the container to indicate when the temperature-calibrated thermoplastic compound has flowed into the waste space to penetrate and encapsulate the mass of waste items therein.

4. Apparatus as set forth in claim 1, including means to apply pressure to the temperature-calibrated compound in its liquid phase to cause it to flow into and around the mass of waste items and to press the plastic against the internal container walls to preclude projection of sharp elements from the surfaces of the encapsulating plastic.

5. Apparatus as set forth in claim 1 including vent means to exhaust air and vapor from the waste space during sterilization and encapsulation 6. Apparatus as set forth in claim 1 including an overflow reservoir for excess liquid plastic carried by the container.

7. Apparatus as set forth in claim 1, said container being formed at least in part by said temperature-calibrated thermoplastic.

8. Apparatus as set forth in claim 6 including deformable reinforcement means surrounding the container to maintain the integrity thereof during the liquid phase and to contain the waste items.

9. Apparatus as set forth in claim 8, the reinforcement means affording deformability of at least part of the container to provide for visible geometric change to indicate completion of sterilization.

10. Apparatus as set forth in claim 1 including resilient means in the container to apply pressure to plastic compound to assist the flow in its liquid phase into the waste mass.

11. Apparatus as set forth in claim 1 at least a portion of the container being deformable said portion when deforming forcing the thermoplastic compound in its liquid phase into the waste mass and thereafter upon solidifying to hold the portion in its deformed condition to afford a visual indication of encapsulation and verification of sterilization.

12. Apparatus as set forth in claim 1, said container being heat resistant and having a melting point substantially exceeding that of the plastic compound 13. Apparatus as set forth in claim 1 including indicia on the container to indicate the hazardous mode prior to movement of the movable portion and to indicate the safe mode thereafter.

14. Apparatus as set forth in claim 1 including in combination an oven to heat the container to liquify the thermoplastic compound, and means in the oven to apply driving forces to the movable portion of the container.

15. Apparatus as set forth in claim 14, said means to drive the movable portion of the container comprising a spring.

16. Apparatus as set forth in claim 14, including gaseous evacuation means in the oven coupled to the container to provide for functions selected from among aspirating waste gases, deforming the container and augmenting the flow of liquid phase thermoplastic to achieve a sterile, void-free mass.

17. Apparatus for sterilizing and encapsulating medical wastes selected from among compressible and incompressible items and meltable and non-meltable items,
   a container having at least two complementary relatively movable parts defining a waste chamber and access means for depositing medical wastes into the chamber,
   a first temperature-calibrated thermoplastic medium to hold the complementary container parts in a first geometrical shape defining an enlarged chamber,
   a second temperature-calibrated thermoplastic medium in the container having a melting temperature below that of the first thermoplastic medium, whereby upon liquefaction by heating the second thermoplastic medium can flow into and among the waste items in the chamber, in a preliminary, treating cycle thereby simultaneously creating additional chamber space for additional waste items and at least partially encapsulating and sterilizing the first charge of waste items, and whereby upon being filled with subsequent waste items to a point approaching substantially the theoretical capacity of the container, heating the container to the liquefaction temperature of the first thermoplastic medium will release the relatively movable container parts, and
   means to relatively displace the container parts to apply encapsulating pressure to the liquefied mass within and to afford a visual indication and verification of performance of the treating cycle.

18. Apparatus as set forth in claim 17, the liquefaction temperature of the first calibrated thermoplastic medium being selected at a value which destroys substantially all biological life substantially on contact.

19. Apparatus as set forth in claim 17, said container having a cylindrical base part, said first and second calibrated thermoplastic media comprising concentric outer and inner sleeves respectively in the base part, and a cover part carried by the outer sleeve and having a telescoping relation to base part when the first thermoplastic medium is liquefied.

20. Apparatus as set forth in claim 17, said first calibrated thermoplastic medium comprising a member to engage the base and cover parts in at least partial locking relationship, said second calibrated thermoplastic medium comprising a liquefiable mass disposed within the container.

21. Apparatus as set forth in claim 17, said relatively movable container parts having an initially exposed surface carrying graphics denoting hazardous wastes, said surface being obliterated when the container parts are relatively displaced after final encapsulation.

22. Apparatus as set forth in claim 17, said relatively movable container parts including vent means to pass gas vapors and liquefied plastic from the waste chamber, said parts defining an overflow reservoir to receive plastic extruded from the chamber.

23. Apparatus as set forth in claim 17, said means to displace the relatively movable container parts comprising weight means.

24. Apparatus as set forth in claim 17, including an oven to receive the container having two operating temperatures corresponding to the respective melting temperatures of the first and second calibrated thermoplastic media.

25. Apparatus as set forth in claim 24, said oven including compression means to impart force to the relatively movable container parts.

26. Apparatus as set forth in claim 24, said waste container including heat resistant base and cover parts, the latter removable to facilitate filling the base part with medical waste items, said oven having a removable cover portion, and releasable means in the oven cover portion to grip the cover part of the container, whereby both can open simultaneously to gain access to the waste container.

27. A method for encapsulating and sterilizing medical wastes comprising the steps of
   a) accumulating successive supplies of waste items in a container,
   b) successively heating the container and a volume of a first thermoplastic compound having a calibrated melting temperature to a molten state,
   c) thereafter causing the molten plastic compound to flow under pressure around and among the waste items to fill all void spaces, and while confining the exterior of the mass to preclude projection of waste implements, and
   d) solidifying the mass to create a substantially sterile mass in which all sharp edges and points are encapsulated against external exposure.

28. The method as set froth in claim 27 in which the melting point of the temperature-calibrated thermoplastic compound corresponds to the temperature at which all biological life, including spore forms, is rendered sterile substantially on contact.

29. The method as set forth in claim 27 using a heat resistant container having a fixed and a movable part defining a cased volume reducible in size by movement thereof, the steps of
   restraining the movement of the part through a succession of waste loading and melting cycles; and
   thereafter releasing the movable container part; and
   applying pressure to the movable part to drive the thermoplastic into the waste to encapsulate the waste in a substantially void free at least partially sterile mass free of projecting waste elements.

30. The method as set forth in claim 29 including the step of restraining the movement of the movable part by means of a second thermoplastic compound having a higher melting temperature than the first thermoplastic compound, and
   releasing the movable part by heating the container at least to the higher temperature.

* * * * *